United States Patent [19]

Cooper

[11] Patent Number: 4,474,995

[45] Date of Patent: Oct. 2, 1984

[54] HYDROFORMYLATION PROCESS EMPLOYING TETRACARBOXYLATODIRUTHENIUM HALIDE COMPLEX CATALYST

[75] Inventor: James L. Cooper, Longview, Tex.

[73] Assignee: Eastman Kodak Company, Rochester, N.Y.

[21] Appl. No.: 411,772

[22] Filed: Aug. 26, 1982

[51] Int. Cl.$^3$ .............................................. C07C 45/50
[52] U.S. Cl. ..................................... 568/451; 568/452
[58] Field of Search ........................ 568/451, 452, 909

[56] References Cited

U.S. PATENT DOCUMENTS 3,965,192  6/1976  Booth ................................. 568/451
4,226,845 10/1980  Laine ................................. 568/451
4,252,678  2/1981  Smith ................................. 568/451
4,306,084 12/1981  Pettit ................................. 568/451

FOREIGN PATENT DOCUMENTS 966432 8/1964 Canada ............................... 568/451

Primary Examiner—Werren B. Lone

Attorney, Agent, or Firm—Donald W. Spurrell; Daniel B. Reece, III

[57] ABSTRACT

Disclosed is a process for the hydroformylation of olefins (includes mixtures of olefins) of 2 to 20 carbons, and preferably of 3 to 10 carbons for the production of relatively high proportions of branched to linear aldehydes, and with especially good selectivity to the production of butyraldehydes from propylene, wherein the olefin is contacted in a reaction zone at a temperature of from about 70° C. to about 250° C., preferably from about 150° C. to about 220° C., and a pressure of from about 500 psig to about 10,000 psig, preferably from about 2,500 psig to about 3,500 psig with hydrogen and carbon monoxide in the presence of a catalytic amount of one or more tetracarboxylatodiruthenium halide complexes, i.e., an amount containing from about $10^{-7}$ to about $10^{-1}$, preferably from about $10^{-5}$ to about $10^{-3}$ moles of ruthenium per mole of olefin, for a sufficient period of time to permit reaction of the olefin with the hydrogen and carbon monoxide to form aldehyde product.

14 Claims, No Drawings

HYDROFORMYLATION PROCESS EMPLOYING TETRACARBOXYLATODIRUTHENIUM HALIDE COMPLEX CATALYST

DESCRIPTION

This invention concerns a hydroformylation process wherein olefin is converted to aldehyde product for use as such or for conversion by known methods to products such as alcohols and acids. More particularly, the invention concerns an oxo process especially suited for the preparation of unusually high proportions of branched aldehydes from α-olefins, particularly isobutyraldehyde from propylene, and mixed valeraldehydes from 1-butene. The isobutyraldehyde may be converted, for example, to 2,2,4-trimethyl-1,3-pentanediol monoisobutyrate useful as a high boiling solvent and coalescing aid for paints and the like.

Heretofore, considerable emphasis for oxo processes has been placed on the production of relatively high ratios of normal to branched aldehyde product, and to this end the catalyst, reactants, and reaction conditions have been selected to give these ratios. See, for example, U.S. Pat. Nos. 3,527,809; 3,917,661; 3,965,192; and 4,148,830. For such processes the catalyst is typically cobalt or rhodium complexed with such materials as carbonyl, phosphines and phosphites. Also, U.S. Pat. No. 3,239,566 discloses the use of a ruthenium oxo catalyst in complex form containing a phosphorus compound ligand for giving a relatively high normal to iso-aldehyde ratio as well as substantial amounts of oxo alcohol, such ruthenium catalyst being, of course, already recognized for its activity in hydrogenations.

Principal objects, therefore, of the present invention are to provide an oxo catalyst system which gives a relatively low normal to branched aldehyde product ratio in high yield, operates effectively over a wide range of conditions of temperature, pressure, and catalyst concentrations, particularly at low catalyst concentrations, and which exhibits special selectivity to producing butyraldehydes from propylene. These and other objects hereinafter appearing have been attained in accordance with the present invention through the use of one or more tetracarboxylatodiruthenium halides in the hydroformylation of olefins to aldehydes, particularly in relatively low ratios of normal to branched aldehyde, e.g., below about 1.5 for propylene feed.

The present invention is more particularly defined as a hydroformylation process comprising contacting olefin (term as used herein means one or more olefins) having from 2 to 20 carbons, preferably 3-10 carbons, and most preferably one or more of ethylene, propylene and 1-butene in a reaction zone at a temperature of from about 70° C. to about 250° C., preferably from about 150° C. to about 220° C., and a pressure of from about 500 psig to about 10,000 psig, preferably from about 2,500 psig to about 3,500 psig, with hydrogen and carbon monoxide, in the presence of a catalytic amount of a tetracarboxylatodiruthenium halide complex, i.e., such as an amount containing from about $10^{-7}$ to about $10^{-1}$, preferably $10^{-5}$ to about $10^{-3}$ moles of ruthenium per mole of said olefin, for a sufficient period of time to permit reaction of said olefin with said hydrogen and carbon monoxide to form aldehyde product. It is particularly noted that the present tetracarboxylatodiruthenium halide complexes may be considered as precursors to the active catalytic species which are derived therefrom in the reactor. The essence of the invention, however, is that the present complexes are fed to the reactor as such and the olefin, $H_2$ and CO come into contact with each other in the presence thereof even though the aforesaid catalytic species forms therefrom.

In the case of propylene feed, the most preferred reaction conditions are temperatures of from about 50° C. to about 190° C., pressures of from about 2,500 psig to about 3,500 psig, and a catalyst concentration of from about $10^{-4}$ to about $8 \times 10^{-4}$ moles of Ru/mole of propylene. It is noted that in continuous hydroformylations the catalyst feed (recycle or make-up) is continuously or periodically adjusted to maintain the desired Ru/olefin ratio in the reaction zone.

The present tetracarboxylatodiruthenium halide complexes have the formula $(R-O)_4Ru_2X$ wherein each R is an independently selected alkanoyl group the size of which is not critical, but preferably is from 2-15 carbons, and X is Cl, Br or I. These R groups are straight or branched and can be substituted with any group which does not adversely affect the reaction. Most preferred R groups are butyryl, isobutyryl, propionyl, isopropionyl and mixtures of any thereof. These complexes may be prepared, for example, by reacting hydrated ruthenium trihalide with the appropriate carboxylic acid-acid anhydride mixture (mixtures for mixed R groups) as taught, for example, by Stephenson and Wilkinson in the "Journal of Inorganic Nuclear Chemistry," 1966, Vol. 28, pp. 2285-2291, Pergamon Press Ltd. In examples 2-10 below, the catalysts were prepared by the following procedure exemplified by tetraisobutyratodiruthenium chloride complex: Into a flask fitted with an overhead stirrer, $N_2$ inlet (for blanketing the reaction medium) and reflux condenser, was placed 1 mole of $RuCl_3$, 3 moles of sodium isobutyrate, and 1-2 liters of water. The mixture was then heated to about 90° C. for 1 hour, cooled, and the precipitate product filtered, washed with water and dried. The product was ready for use in the hydroformylation reaction.

In carrying out the hydroformylation in known continuous manner, conventional oxo equipment and procedures may be employed, such as an overflow reactor, the catalyst leaving the reaction zone with the product aldehyde, the product solution then passed through a series of vapor liquid separators, the gases being recycled to the reactor, and the liquid let down to atmospheric pressure by conventional techniques. This liquid comprising a mixture of aldehyde products, solvent, and catalyst may then be passed through a distillation column to remove aldehydes overhead, and the catalyst with high boiling base effluent recycled back to the reactor through suitable pressure pumping means.

In such a continuous process, the syn gas ($H_2$+CO) is introduced into the reactor in a continuous manner by means, for example, of a primary compressor, and the ratio of hydrogen to carbon monoxide in the feed may be selected according to the particular olefin being hydroformylated and the selected reaction conditions, as is well known in the art. Generally, the molar ratio of hydrogen to carbon monoxide in the reactor is maintained within the range of above about 0.5 to about 4.0, but it has been found in many hydroformylations that the rate of reaction as well as yield of the desired product may be increased by increasing the hydrogen to carbon monoxide molar ratio to above 4.0, and even up to about 10.0 or more. The molar ratio of syn gas (total moles of $H_2$+CO) to olefin typically is maintained in the reaction zone at from about 0.5 to about 20, and preferably from about 1.2 to about 6.

The olefin is fed to the reactor by means of suitable pumps capable of operating under substantial pressures and the feed rates of the olefin and syn gas are selected to maintain the above-recited molar ratios of these reactants in the reactor. Typical useful olefins contain from 2 to 20 carbon atoms and preferably from 3 to 10 carbon atoms, straight-chain or branched-chain, and optionally containing groups or substituents which do not interfere with the hydroformylation process. Such olefins are ethylene, propylene, 1-butene, 2-methyl propylene, 2-methyl-1-butene, 1-pentene, 1-hexene, 1-heptene, 1-octene, 2-ethyl-1-hexene, 1-dodecene and 1-octadecene. Also useful in the present process are the internal olefins such as butene-2 and cyclic olefins such as cyclooctene. If desired, mixtures of olefins can be fed to the reactor.

Any suitable solvent which does not adversely affect the process and which is inert with respect to the catalyst, olefin, syn gas and the hydroformylation products may be used. Inert solvents of this nature are well known in the art and include benzene, xylene, toluene and their substituted derivatives, pentanes, naphtha, kerosene, mineral oils, cyclohexane, cyclopentane, ethers, esters, etheresters, alcohols, acetals, ketones, and various mixtures thereof. Preferred solvents include 2,2,4-trimethyl-1,3-pentanediol monoisobutyrate (TMPDMI), and its isomers, and the by-products such as alcohols, esters, acetals, and hydroxyaldehydes produced in the hydroformylation reaction and retained as high boiling liquids at the bottom of the distillation column.

This invention is illustrated further by the following examples although it will be understood that these examples are included merely for purposes of illustration and are not intended to limit the scope of the invention unless otherwise specifically indicated. Example 1 is for comparison purposes and utilizes a known catalyst, triruthenium dodecacarbonyl. In all of the examples below, the reactor pressure was maintained by adjusting, as necessary, the rate of syn gas feed to the reactor (autoclave).

EXAMPLE 1

Propylene (2.14 moles) was placed in a high pressure reactor (autoclave) containing toluene (100 ml) and triruthenium dodecacarbonyl in an amount giving $4.38 \times 10^{-3}$ moles of Ru/mole of propylene. A mixture of hydrogen and carbon monoxide in a 1/1 mole ratio was pressured at 1,600 psig into the reactor, the temperature raised to 170° C., and the reactor pressure adjusted to and maintained at 2,500 psig throughout the 2.0-hour run. Analysis of the liquid product by gas-liquid chromatography showed the catalyst selectivity to butyraldehyde to be 77.04 percent, a linear to branched aldehyde product ratio of 2.05, and an aldehyde production rate of 2.3 pounds per cubic foot-hour.

The following examples 2 through 10 illustrate the exceptional utility of the present ruthenium complexes, within a range of operating parameters, for the hydroformylation of propylene to markedly low linear to branched aldehyde product ratio as compared, for example, to that obtained with triruthenium dodecacarbonyl. In each of these examples, propylene (0.95 mole) was placed in a 300 ml high pressure stainless steel autoclave which contained toluene (100 ml) and the tetracarboxylatodiruthenium halide in an amount giving $4.25 \times 10^{-4}$ moles of Ru/mole of propylene, i.e., 400 ppm of ruthenium for the 0.95 moles of propylene. A mixture of hydrogen and carbon monoxide in a mole ratio of 1/1 was pressured at 2,000 psig into the autoclave at room temperature and the temperature raised to that specified, the pressure increasing to the desired psig. This pressure was maintained throughout the 30-minute run time by syn gas feed as aforesaid. The products and their distributions were determined by gas-liquid chromatography.

The runs of examples 3 through 10 were conducted according to the general procedure of example 2. Reaction conditions and results for these examples are given in Tables 1 and 2. Examples 3, 9, and 10 illustrate the differences in activity and product selectivity of the chloride, bromide, and iodide versions of the present catalysts.

TABLE 1

| Example No. | PPM Ruthenium[a] | Reaction Conditions Temp., °C. | Press., psig | Production Rate, lb/ft³-hr. | Product Distribution |  |  |
|---|---|---|---|---|---|---|---|
|  |  |  |  |  | HBu N/I[b] | % HBu[d] | BuOH[c] |
| 2 | 400 | 150 | 2,500 | 5.45 | 1.19 | — | — |
| 3 | 400 | 170 | 2,500 | 20.10 | 1.14 | 98 | 0 |
| 4 | 400 | 190 | 2,500 | 30.19 | 1.18 | 94 | 6 |
| 5 | 400 | 210 | 2,500 | 31.20 | 1.16 | 84 | 16 |
| 6 | 400 | 170 | 3,500 | 26.50 | 1.15 | 100 | 0 |
| 7 | 400 | 190 | 3,500 | 38.60 | 1.19 | 98 | 2 |
| 8 | 400 | 210 | 3,500 | 41.40 | 1.16 | 94 | 6 |

[a]Charged as tetraisobutyratodiruthenium chloride.
[b]Normal to isobutyraldehyde ratio.
[c]Butanol (BuOH)
[d]Butyraldehyde (HBu)

TABLE 2

| Example No. | Catalyst | Reaction Conditions Temp., °C. | Press., psig | Production Rate, lb/ft³-hr. | Product Distribution % HBu | BuOH | HBu N/I |
|---|---|---|---|---|---|---|---|
| 9 | (isobutyryl-O)₄Ru₂I 400 ppm Ru | 170 | 2,500 | 5.3 | 100 | 0 | 1.03 |
| 10 | (isobutyryl-O)₄Ru₂Br 400 ppm Ru | 170 | 2,500 | 17.8 | 95.6 | 4.4 | 1.24 |
| 3 | (isobutyryl-O)₄Ru₂Cl 400 ppm Ru | 170 | 2,500 | 20.1 | 98.0 | 2.0 | 1.14 |

The invention has been described in detail with particular reference to preferred embodiments thereof, but it will be understood that variations and modifications can be effected within the spirit and scope of the invention.

I claim:

1. A hydroformylation process for the production of low ratio, normal to branched aldehyde product, comprising contacting olefin in a reaction zone at a temperature of from about 70° C. to about 250° C., and a pressure of from about 500 psig to about 10,000 psig, with hydrogen and carbon monoxide in the presence of a catalytic amount of one or more complexes of the formula $(R-O)_4Ru_2X$ wherein each R is an independently selected alkanoyl group, and X is Cl, Br, or I, for a sufficient period of time to permit reaction of the olefin with the carbon monoxide and hydrogen to form aldehyde product.

2. The process of claim 1 wherein the reaction temperature is from about 150° C. to about 220° C., the pressure is from about 2,500 psig to about 3,500 psig, and in the formula $(R-O)_4Ru_2X$, each R is an independently selected alkanoyl group of 2–15 carbons.

3. The process of claim 2 wherein R is butyryl, isobutyryl, propionyl, isopropionyl, or mixtures thereof, and X is Cl.

4. The process of claim 1 wherein the moles of ruthenium per mole of olefin is from about $10^{-5}$ to about $10^{-3}$.

5. The process of claim 2 wherein the moles of ruthenium per mole of olefin feed is from about $10^{-5}$ to about $10^{-3}$.

6. The process of claim 3 wherein the olefin is one or more of ethylene, propylene and 1-butene.

7. The process of claim 1 wherein the catalyst is tetraisobutyratodiruthenium chloride complex.

8. The process of claim 1 wherein the catalyst is tetraisobutyratodiruthenium bromide complex.

9. The process of claim 1 wherein the catalyst is tetraisobutyratodiruthenium iodide complex.

10. The process of claim 1 wherein the molar ratio of $H_2$ to carbon monoxide in said reaction zone is from about ½ to about 4/1.

11. The process of claim 10 wherein said ratio is from about 1.5/1 to about 1/1.5.

12. The process of claim 10 wherein said olefin is propylene and the ratio of normal to isobutyraldehyde product is below about 1.5.

13. The process of claim 3 wherein the catalyst is tetraisobutyratodiruthenium chloride complex.

14. The process of any one of claims 1–5 and 7 wherein the olefin is propylene and the ratio of normal to isobutyraldehyde product is below about 1.5.

* * * * *